(12) United States Patent
Carriazo (10) Patent No.: US 10,772,763 B2
(45) Date of Patent: Sep. 15, 2020

(54) TREATMENT APPARATUS FOR CORRECTING A REFRACTIVE ERROR OF AN EYE

(71) Applicant: Cesar C. Carriazo, Barranquilla (CO)

(72) Inventor: Cesar C. Carriazo, Barranquilla (CO)

( * ) Notice: Subject to any disclaimer, the term of this patent is extended or adjusted under 35 U.S.C. 154(b) by 182 days.

(21) Appl. No.: 14/840,822

(22) Filed: Aug. 31, 2015

(65) Prior Publication Data

US 2017/0056246 A1    Mar. 2, 2017

(51) Int. Cl.
*A61F 9/008* (2006.01)

(52) U.S. Cl.
CPC ............ *A61F 9/00804* (2013.01); *A61F 2009/00857* (2013.01); *A61F 2009/00872* (2013.01); *A61F 2009/00893* (2013.01)

(58) Field of Classification Search
CPC ... A61F 9/0079; A61N 5/0613; A61N 5/0624; A61N 2005/0643; A61N 2005/0648; A61N 2005/067; A61N 2005/0626; A61N 2005/0647; A61N 2005/0652; A61N 2005/0659; A61N 2005/0662; A61M 37/00; A61M 2037/0007
USPC ..................... 607/88–92; 606/2–19
See application file for complete search history.

(56) References Cited

U.S. PATENT DOCUMENTS

| | | | | |
|---|---|---|---|---|
| 4,856,513 A * | 8/1989 | Muller | ............ | A61F 9/008 219/121.6 |
| 5,152,759 A * | 10/1992 | Parel | ............ | A61F 9/008 606/17 |
| 5,314,422 A * | 5/1994 | Nizzola | ............ | A61F 9/008 606/17 |
| 5,711,762 A * | 1/1998 | Trokel | ............ | A61F 9/008 606/16 |
| 6,059,775 A * | 5/2000 | Nielsen | ............ | A61F 9/008 606/4 |
| 2003/0128334 A1* | 7/2003 | O'Donnell, Jr. | ..... | A61F 9/00804 351/209 |

(Continued)

FOREIGN PATENT DOCUMENTS

| | | |
|---|---|---|
| DE | 102013219788 A1 | 4/2015 |
| WO | 2008055706 A1 | 5/2008 |

OTHER PUBLICATIONS

Girard, Louis J., "Corneal Surgery: Advanced Techniques in Ophthalmic Microsurgery", The C. V. Mosby Company, vol. Two, 149-153.*

*Primary Examiner* — Michael W Kahelin
*Assistant Examiner* — Vynn V Huh
(74) *Attorney, Agent, or Firm* — Barlow, Josephs & Holmes, Ltd.

(57) ABSTRACT

The invention relates to treatment apparatus (10) for correcting a refractive error of an eye (12) that includes a laser device (14) for separating corneal tissue by means of laser radiation (16); a control device (18) designed to control the laser device (14) to emit the laser radiation (16) for cutting out and/or ablating a volume (24) out of the surface (26) of the cornea (22) of the eye (12) in dependency on a measured pachymetry of the cornea (22) and the refractive error of the eye (12), whereby the cut-out and/or ablated volume (24) in the surface (20) of the cornea (22) results in a shape of a closed ring, a partial ring, a crescent or a crescent shaped closed ring. A method for controlling such an apparatus for correcting a refractive error of an eye, and to a protective mask for an eye are also provided.

9 Claims, 13 Drawing Sheets

(56) References Cited

U.S. PATENT DOCUMENTS

2006/0015090 A1\* 1/2006 Roberts ............... A61F 9/008
  606/5
2008/0287928 A1 11/2008 Arnoldussen et al.
2010/0249761 A1 9/2010 Ruiz et al.
2010/0331831 A1 12/2010 Bischoff et al.
2014/0135748 A1\* 5/2014 Dai ................. A61F 9/00814
  606/5

\* cited by examiner

Fig.17

TREATMENT APPARATUS FOR CORRECTING A REFRACTIVE ERROR OF AN EYE

FIELD OF THE INVENTION

The invention relates to a treatment apparatus for correcting a refractive error of an eye, a method for controlling a treatment apparatus for correcting a refractive error of an eye, a method for correcting a refractive error of an eye, and a protective mask for an eye.

BACKGROUND OF THE INVENTION

US 2010/0331831 A1 discloses a treatment apparatus for operatively correcting myopia or hyperopia in an eye. The treatment apparatus includes a laser device controlled by a control device, which is used to separate corneal tissue of the eye by applying a laser beam. In order to minimize a regression of a corrected visus of the eye over time, it is suggested to cut a lenticule-shaped volume from within the cornea of the eye. This lenticule-shaped volume has a minimum thickness in order to be able to safely remove all corneal tissue cut out of the cornea. The minimum thickness thus reduces complications during and after a corrective surgical procedure for correcting the reflective error of the eye.

A refractive error of an eye can especially occur due to a degenerative disorder of the eye, especially due to the degenerative disorder called keratoconus. This degenerative disorder of the eye causes structural changes within the cornea, which cause it to thin and change to more conical shape. This change of the shape can also be called a keratoconus and can cause substantial distortion of the vision.

There are several methods known for correcting the refractive error of an eye due to the keratoconus. The Wikipedia article "Keratoconus", dated Aug. 19, 2015, gives a good overview for possible corrections of refractive errors due to a keratoconus. One possibility is the insertion of intrastromal corneal ring segments. This procedure requires to make a small incision in the periphery of the cornea and to slide two thin arcs of polymethyl methacrylat between the lays of the stroma on either side of the pupil. Afterwards, the incision is closed by a suture. However, such an implant can cause both complications during the surgical operations and afterwards. For example, the implant can cause an inflammation of the eye, possibly permanently damaging the eye. Furthermore, the implants can grow out of the cornea. Additionally, due to the implant, the eye is much more suspectible for a trauma from an external object impacting acting on the eye.

Furthermore, the Wikipedia article suggests that a LASIK procedure for correcting the refractive error of the eye is contra-indicated in keratoconus and other corneal thinning conditions as removal of corneal stroma tissue will further damage an already thin and weak cornea. This is especially the case for the method suggested in US 2010/0331831 A1, as it requires a minimum thickness of the corneal tissue volume removed.

It is an object of the present invention to provide a treatment apparatus for correcting a refractive error of an eye that is especially gentle to the cornea of the eye. Furthermore, it is an object of the present invention to provide a method for controlling a treatment apparatus for correcting a refractive error of an eye that allows for an especially gentle treatment of the eye. Furthermore, it is an object of the present invention to provide a method for correcting a refractive error of an eye that is especially gentle for the cornea of the eye. Another objective of the present invention is to provide a protective mask for the eye that can reduce the risk of complications when correcting a refractive error of the eye.

BRIEF SUMMARY OF THE INVENTION

According to embodiments of the invention described herein, these objects are solved by a treatment apparatus, a method for controlling a treatment apparatus, a method for correcting a refractive error of an eye, and a protective mask according to the present invention. Advantageous embodiments with expedient developments of the invention are specified below.

A first aspect of the invention concerns a treatment apparatus for correcting a refractive error of an eye. This treatment apparatus comprises a laser device for separating corneal tissue by means of laser radiation. For example, this laser device can be designed as a so called femtosecond laser device. Such a laser device only emits laser radiation for very short time burst. Another example for the laser device is an excimer laser. Furthermore, the treatment apparatus comprises a control device designed to control the laser device to emit the laser radiation for cutting out and/or ablating a volume out of the surface of the cornea of the eye in dependency on a measured pachymetry of the cornea and the refractive error of the eye, whereby the cut-out and/or ablated volume of the surface of the cornea results in a shape of a closed ring, a partial ring, a crescent or a crescent shaped closed ring. Afterwards, the volume that has been cut out and/or ablated out of the surface of the cornea can be closed by a suture. This leads to a reduction in a radius of the cornea of the eye and an at least partial correction of the refractive error of the eye. In other words: The lens that is constituted by the cornea is flattened due to the volume cut-out of the cornea and subsequent stretching of it surface. This leads to at least a partial correction of the refractive error in the eye, especially a refractive error due to a keratoconus. The control device can be designed as an automatic control device. This means there is no manual input necessary for controlling the laser device once a treatment procedure has been started.

The treatment apparatus allows correcting the refractive error of the eye with a method that is especially gentle to the cornea of the eye. There is no need to remove a volume with a minimum thickness from the cornea of the eye. As there are no minimum requirements to the thickness of the volume to be removed, an especially small and/or thin volume can be removed. This means that the treatment apparatus can still be used for eyes whose corneas are especially thin due to a degenerative disorders.

Furthermore, a treatment of the eye with the treatment apparatus does not require inserting any implants into the cornea of the eye in order to at least partially correct the refractive error. This also means that there is no risk of complications which are usually associated with such implants.

Furthermore, the geometry of the volume that results in a shape of a closed ring, a partial ring, a crescent, or a crescent shaped closed ring in the surface of the cornea is especially advantageous for an especially thin cornea. Instead of removing a whole area of circle, only a closed or a partial ring, or a crescent is cut out of the surface. This means that an especially small volume is cut out of the cornea. The partial ring also allows correcting astigmatism, shifting a visual axis of the cornea and/or shifting a peak of a keratoconus. A crescent shape and/or a crescent shaped closed ring allows accounting for an asymmetrical refractive error and/or an asymmetrical thinning of the cornea. Furthermore, any crescent shape allows reducing tension peaks in the cornea of the eye when closing the cut out volume by a suture. The ends of the cut out volume in a circumferential direction on the surface of the cornea are preferably tapered, avoiding any tension peaks.

In this description, for purposes of simplicity, any volume cut out and/or ablated can simply be called cut out volume and/or removed volume.

In a further advantageous configuration of the treatment apparatus, the treatment apparatus comprises a pachymeter for measuring the pachymetry of the cornea. This allows measuring the pachymetry of the eye immediately before starting a surgical procedure. Furthermore, as the pachymetry of an eye with keratoconus can rapidly change over time, any influence due to a change over time of the cornea should be minimized. This pachymeter also allows for online correction and/or monitoring of the procedure for correcting the refractive error of the eye.

In a further advantageous configuration of the treatment apparatus, the treatment apparatus comprises a tonometer for determining an intraocular pressure of the eye, whereby the volume to be cut out and/or ablated is determined in dependency on the determined intraocular pressure. The information about the intraocular pressure can be used to determine which parts of the cornea can withstand the highest tension and/or where the most volume can be cut out of the cornea without risking the structural integrity of the cornea. This allows locating the volume to be cut out and/or ablated of the cornea in an area of the cornea where its removal is the least stressful to the eye.

In a further advantageous configuration of the treatment apparatus, the volume to be cut out and/or ablated is determined by an evaluation device of the treatment apparatus in dependency of the measured pachymetry of the cornea and the refractive error of the eye. The evaluation device can be part of the control device. This allows for easy automation of the procedure to correct the refractive error of the eye. The evaluation device is especially advantageous if the treatment apparatus also comprises the pachymeter, as no other device has to be used in order to be able to start and/or complete the surgical procedure for correction the refractive error of the eye.

In a further advantageous configuration of the treatment apparatus the volume to be cut out and/or ablated is located outside of a pupil area of the eye. This location of the volume to be cut out and/or ablated is especially advantageous, as sutures and/or scars in this area outside of the pupil have an especially low impact on the vision and/or visus of the patient. Furthermore, this location of the volume to be removed is in area where the impacts of a keratoconus are usually especially low. Here it can be expected that the cornea is still especially thick. The volume to be removed can be located outside the pupil because it is removed out of the surface of the eye. The refractive error of the eye is corrected by suturing the cornea where the volume has been removed, stretching the surface of the cornea, thus flatting the cornea. The location outside the pupil area is possible as the refractive error of the eye is not corrected by reshaping the lenticular shape of the cornea itself by removing a volume but instead by changing tensions in the surface of the cornea and/or reducing the surface of the cornea.

In a further advantageous configuration of the treatment apparatus, the volume to be cut out and/or ablated is located with equidistance to a visual axis of the eye with a cut side of the volume facing the visual axis or with a symmetry axis of the volume. The volume to be cut out and/or ablated is located with equidistance to the visual axis of the eye with the cut side of the volume facing the visual axis especially in the case of a closed or partial ring. The volume to be cut out and/or ablated is located with equidistance to the visual axis of the eye with the symmetry of the volume especially in the case of a crescent shape and/or a crescent shaped closed ring. This allows for an especially even distribution of additional tension in the cornea of the eye, thus being especially gentle for the cornea. Furthermore, this allows correcting the visus of the eye especially well.

Furthermore, a depth of the volume to be cut out and/or ablated can relate to a width of the volume to be cut out and/or ablated in each section. This means, the wider the volume is in a certain section, the deeper it is to be cut out and/or ablated from the cornea in relation to the surface of the cornea. This allows removing a maximum volume without any tension peaks in the cornea of the eye. Alternatively, the volume can have a constant depth. This minimizes the risk of further damaging a cornea that is already especially thin. Preferably, the depth of the volume is also tapered to reduce stress, tension and/or loads for the cornea. That means when viewed from the surface of the cornea, the volume is deeper in the middle and shallower on the sides.

A second aspect of the invention concerns a method for controlling a treatment apparatus for correcting a refractive error of an eye. Preferably, this treatment apparatus is the treatment apparatus according to the first aspect of the invention. The features and advantages described above in connection with the first aspect of the invention apply in a similar manner to the second aspect of the invention. The reverse is also true.

The method according to the second aspect of the invention comprises as a step the measuring of the pachymetry of the cornea of the eye. A volume to be cut out and/or ablated out of the surface of the cornea of the eye is determined in dependency on the measured pachymetry of the cornea and the refractive error of the eye by means of a laser device, whereby the cut out and/or ablated volume in the surface of the cornea results in a shape of a closed ring, a partial ring, a crescent, or a crescent shaped closed ring. The refractive error of the eye can also be determined in dependency of the pachymetry of the cornea. This method for controlling the treatment apparatus results in an especially gentle procedure for the cornea of the eye.

In a further advantageous configuration of the method for controlling the treatment apparatus, the volume to be cut out and/or ablated is determined in dependency of a resulting visus of the eye being above a certain threshold visus. This allows determining the volume in such a way, that the refractive error of the eye is corrected to an acceptable degree. This is especially important for a keratoconus, as a maximum correction of the refractive error of the eye could lead to the determination of a volume to be cut out and/or ablated that is too large for the degenerated and thus especially thin cornea.

In a further advantageous configuration of the method for controlling the treatment apparatus, the volume to be cut out and/or ablated is determined in dependency of a resulting tension in the cornea of the eye being below a certain threshold tension. This allows determining a volume, whose cutting out and/or ablating of the surface of the cornea is especially gentle for the cornea. With such a method it can especially be avoided to increase the tension, stress and or loads in the cornea of the eye by cutting and/or ablating corneal tissue to such a degree that tears or other damage in the cornea could occur, especially after further degeneration of the cornea.

It is especially advantageous to combine the threshold value for the visus and the threshold value for the tension. This allows the volume to be optimized with consideration both to a resulting visus and safety of the cornea and eye.

A third aspect of the invention concerns a method for correcting a refractive error of an eye by means of a treatment apparatus. This can also be called a surgical method and/or surgical procedure. Preferably, the treatment apparatus is the treatment apparatus according to the first aspect of the invention. Preferably, the treatment apparatus is controlled according to a method according to the second aspect of the invention. The features and advantages described above in connection with the first aspect and the second aspect of the invention apply in a similar manner to the third aspect of the invention. The reverse is also true.

For the third aspect of the invention, the pachymetry of the cornea of the eye is measured. A volume to be cut out and/or ablated out of a surface of the cornea of the eye is determined in dependency on the measured pachymetry of the cornea and the refractive error of the eye by means of a laser device, whereby the cut out and/or ablated volume in the surface of the cornea results in a shape of a closed ring, a partial ring, a crescent, or crescent shaped closed ring. The laser device is controlled by means of a control device to emit laser radiation to cut and/or ablate the volume out of the surface of the cornea. This method is especially gentle for the cornea of the eye.

Before the emitting of the laser radiation is started, the eye is preferably anesthetized by anesthetic drops. This increases comfort for the patient and can further reduce unwanted eye movement during the procedure.

In a further advantageous configuration of the method for correcting the refractive error of the eye, the cut out and/or ablated volume in the cornea of the eye is closed by means of suturing at least two opposite sides of the cornea which are bordering the cut out and/or ablated volume together, thus reducing a radius of the cornea. This reduction of the radius of the cornea leads to at least a partial correction of the refractive error of the eye, whereby this correction is especially gentle for the cornea. The suturing of the cornea closes the volume that has been cut out and/or ablated out of the surface of the cornea. After the cuts and/or ablation have been healed, the sutures can be removed from the cornea.

In a further advantageous configuration of the method for correcting the refractive error of the eye, a protective mask with an opening, whereby the opening corresponds to the shape resulting in the surface of the cornea due to the cut-out and/or ablated volume, is placed on the cornea of the eye before the laser radiation is emitted to cut and/or ablate the volume out of the surface of the cornea. Due to the protective mask, the eye and/or its cornea is protected from the laser radiation in the area where no cutting and/or ablation is intended. For this purpose, the protective mask may be aligned with a pupil of the eye. Any laser radiation that hits the protective mask is scattered and/or absorbed in such a way, that it does not cut and/or ablate the underlying cornea. This protects the eye from damage due to laser radiation aimed at a wrong section of the eye and/or due to unwanted eye movement. Furthermore, the laser radiation can possibly be less focused and/or be controlled less precisely. It can be sufficient to aim with a reduced precision and/or with a less focused laser radiation at the opening in the mask and still achieve a precise cut-out and/or ablated volume due to the opening having the desired shape.

A fourth aspect of the invention concerns a protective mask for an eye comprising at least one opening, whereby the opening corresponds to the shape resulting in the surface due to the cut-out and/or ablated volume. The protective mask is designed be used for a method for correcting a refractive error of an eye according to the third aspect of the invention. The protective mask can be used together with a treatment apparatus according to the first aspect of the invention, which can be controlled by a method according to the second aspect of the invention. The features and advantages described above in connection with the first aspect, the second aspect and third aspect of the invention apply in a similar manner to the fourth aspect of the invention. The reverse is also true.

For example, the mask can comprise a plastic material. This plastic material can be designed to at least partially scatter and/or absorb laser radiation emitted by a laser device. This laser device can be the laser device of the treatment apparatus according to the first aspect of the invention. The protective mask can reduce the risk of complications during a surgical procedure for correcting a refractive error of the eye. The protective mask can be similar to a contact lens and can also be placed in a similar way on the eye.

Usually, the protective mask is removed before suturing the eye. The side of the mask being in contact with the eye can have a generic shape. A generic shape results in a very low-cost protective mask. It is also possible to custom shape this side to fit a topography of the eye and/or its cornea. Such a protective mask is especially comfortable for the patient and can adhere especially well to the eye. This can specifically be required if the protective mask shall adhere to an eye with a keratoconus, because in this case the eye can have a highly irregular shaped and/or very conical shaped cornea.

BRIEF DESCRIPTION OF DRAWINGS

The foregoing and further advantages, features and details of the invention are apparent from the following description of preferred embodiments as well as illustrated in the accompanying drawings. The accompanying drawings, which are incorporated herein and form a part of this implication, further serve to explain the principles of the invention and to enable a person skilled in the pertinent art to make and use the invention.

DETAILED DESCRIPTION OF THE INVENTION

Specific embodiments of the present invention are now described with reference to the figures. The following detailed description is nearly exemplary in nature and is not intended to limit the invention or the implication and uses of the invention.

Figure 1:
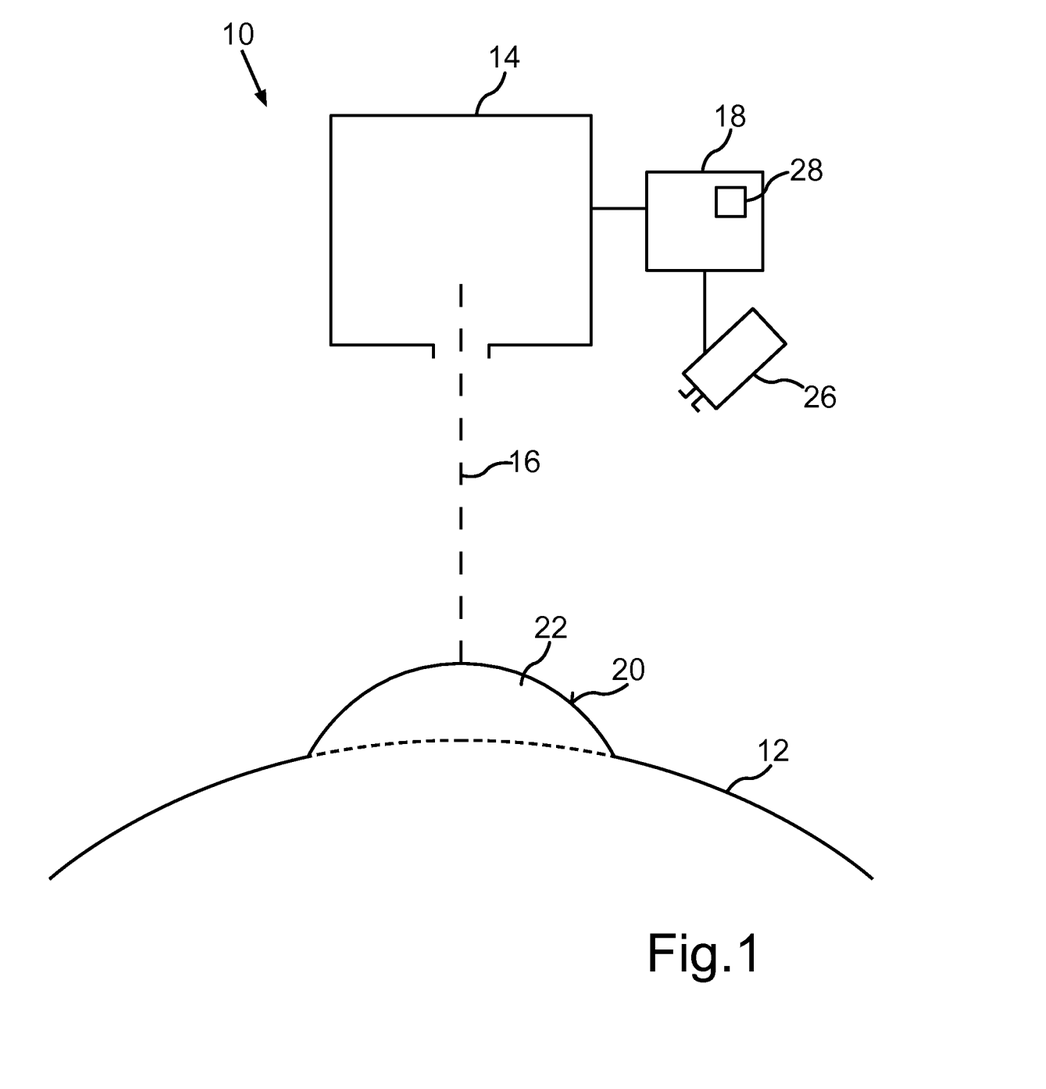
FIG. 1 shows in a schematic view a treatment apparatus for correcting a refractive error of an eye.
Figure 2:
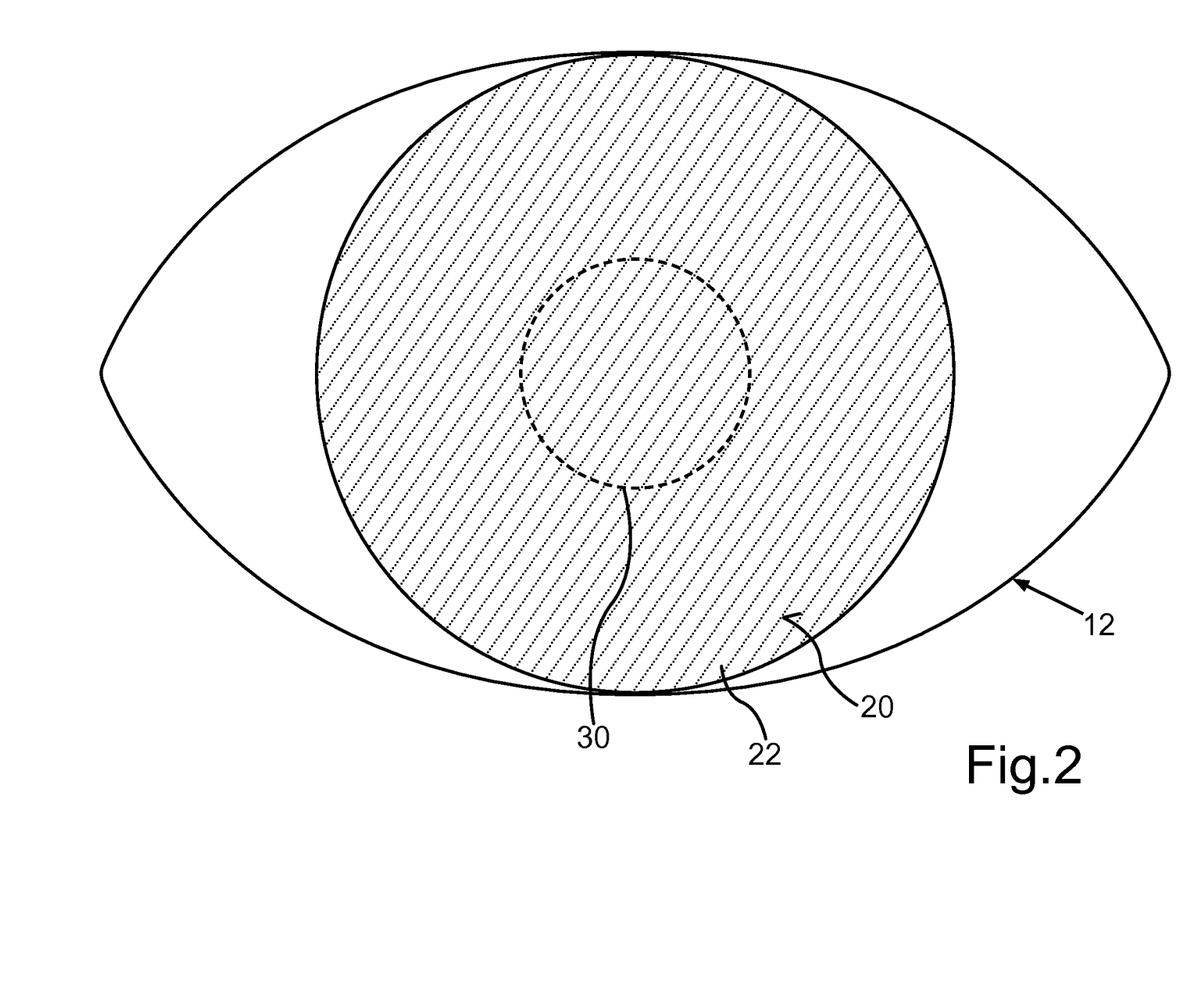
FIG. 2 shows in a schematic view an eye whose refractive error is to be corrected.

FIG. 1 shows in a schematic view a treatment apparatus 10 for correcting a refractive error of an eye 12, which is shown in the schematic view of FIG. 2. The treatment apparatus 10 comprises a laser device 14 for separating corneal tissue by means of laser radiation 16. Furthermore, the treatment apparatus 10 comprises a control device 18 designed to control the laser device 14 to emit the laser radiation 16 for cutting out and/or ablating a volume 24 out of the surface 20 of the cornea 22 of the eye 12 in dependency on a measured pachymetry of the cornea 22 and the refractive error of the eye 12, whereby the cut out and/or ablated volume 24 in the surface 20 of the cornea 22 results in a shape of a closed ring, a partial ring, a crescent or a crescent shaped closed ring. Different examples of a shape of the volume 24 to be cut out and/or ablated are shown in each schematic view of the eye 12 according to FIGS. 3 to 7. For example, the control device 18 can control where the laser device 14 cuts out and/or ablates the volume 24 out of the cornea 22 by adjusting an angle of a reflective mirror inside the laser device 14 and/or by adjusting the focal point of the laser radiation 16.

Furthermore, the treatments apparatus 10 comprises a pachymeter 26 for measuring the pachymetry of the cornea 22. This allows measuring the pachymetry immediately before starting the procedure to cut out and/or ablate the volume 24 out of the cornea 22. The volume 24 to be cut out and/or ablated out of the surface 20 of the cornea 22 is determined by an evaluation device 28 of the treatment apparatus 10 in dependency on the measured pachymetry of the cornea 22 and the refractive error of the eye 12, whereby the refractive error of the eye 12 can also be determined in dependency of the measured pachymetry. In the example shown in FIG. 1, the evaluation device 28 is part of the control device 18. This allows for an automatic surgical procedure by the treatment apparatus 10 that only has to be supervised by a medical specialist.

FIG. 2 shows the eye 12 in a schematic front view. Within the center of the cornea 22, a pupil 30 is located. The eye 12 shown in FIG. 2 has a degenerative disorder called keratoconus. The degenerative disorder keratoconus leads to unwanted structural changes within the cornea 22, causing it to thin and to change to a more conical shape. This can result in a distortion of vision and reduction of visus. However, the thinning of the cornea 22 results in the eye 12 being very sensitive to surgical procedures. Any surgical operation done on the cornea 22 has to be especially gentle in order to not further damage the cornea 22.

FIGS. 3 to 7 show several examples of a volume 24 to be cut and/or ablated out of the cornea 22, which are especially gentle for the cornea 22. The volume 24 is always cut out and/or ablated out of the surface 20 of the cornea 22 by the treatment apparatus 10. The cutting of a volume 24 out of the surface 20 of the cornea 22 does not require a minimum thickness of the volume 24. This allows removing an especially small volume 24 from the cornea 22 in order to at least partially correct the refractive error of the eye 12. Furthermore, as not a lenticular shaped volume of the cornea 22 is removed, any removal of corneal tissue is preferably located outside the pupil 30. Due to such a location, sutures and/or scars cannot further distort the vision of the eye 12. The shape of the cornea 22 itself is not changed by the removal of the volume 24, but rather an area of the surface 20 of the cornea 22 is reduced, leading to a flattening of a radius of the eye 12 due to stretching of the remaining corneal surface tissue.

Figure 3:
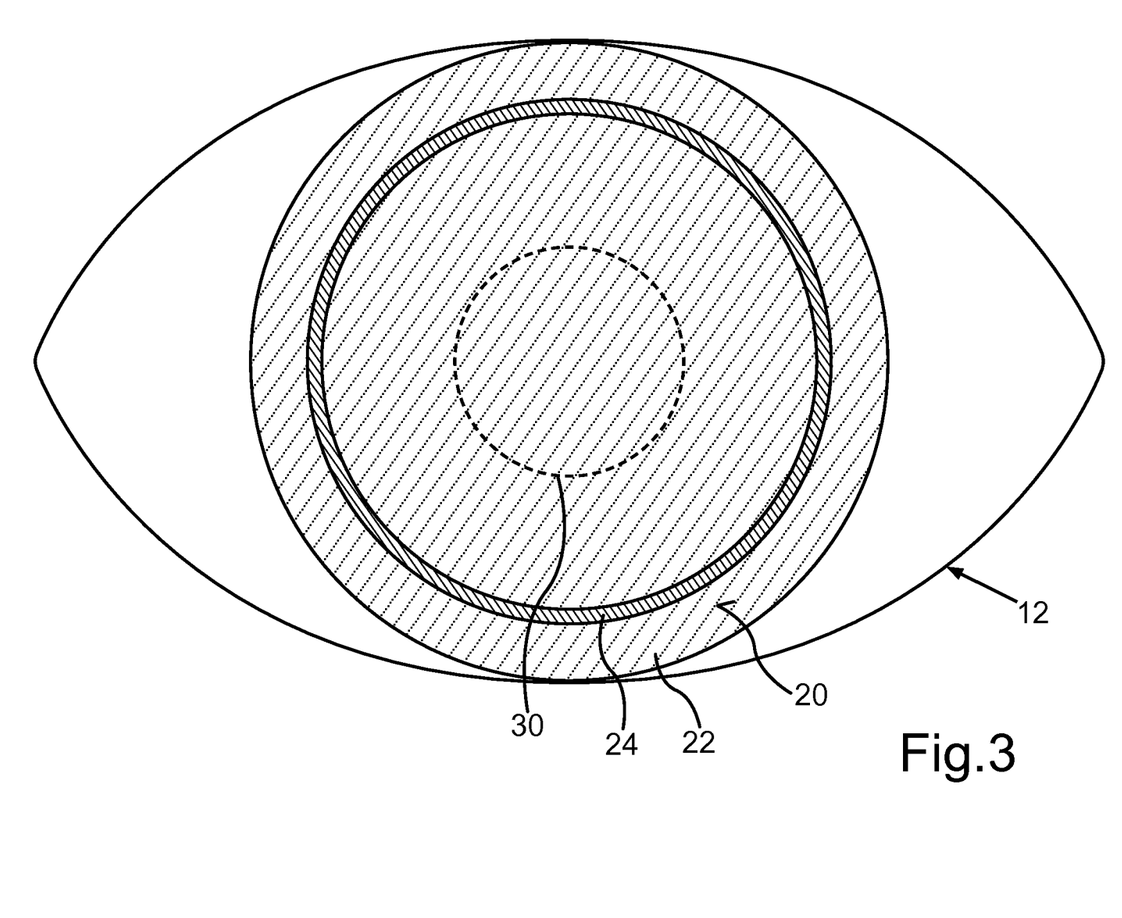
FIGS. 3 to 7 each show in a schematic view a different shape of a volume to be cut out and/or ablated out of the surface of the eye according to FIG. 2 in order to correct its refractive error.
Figure 4:
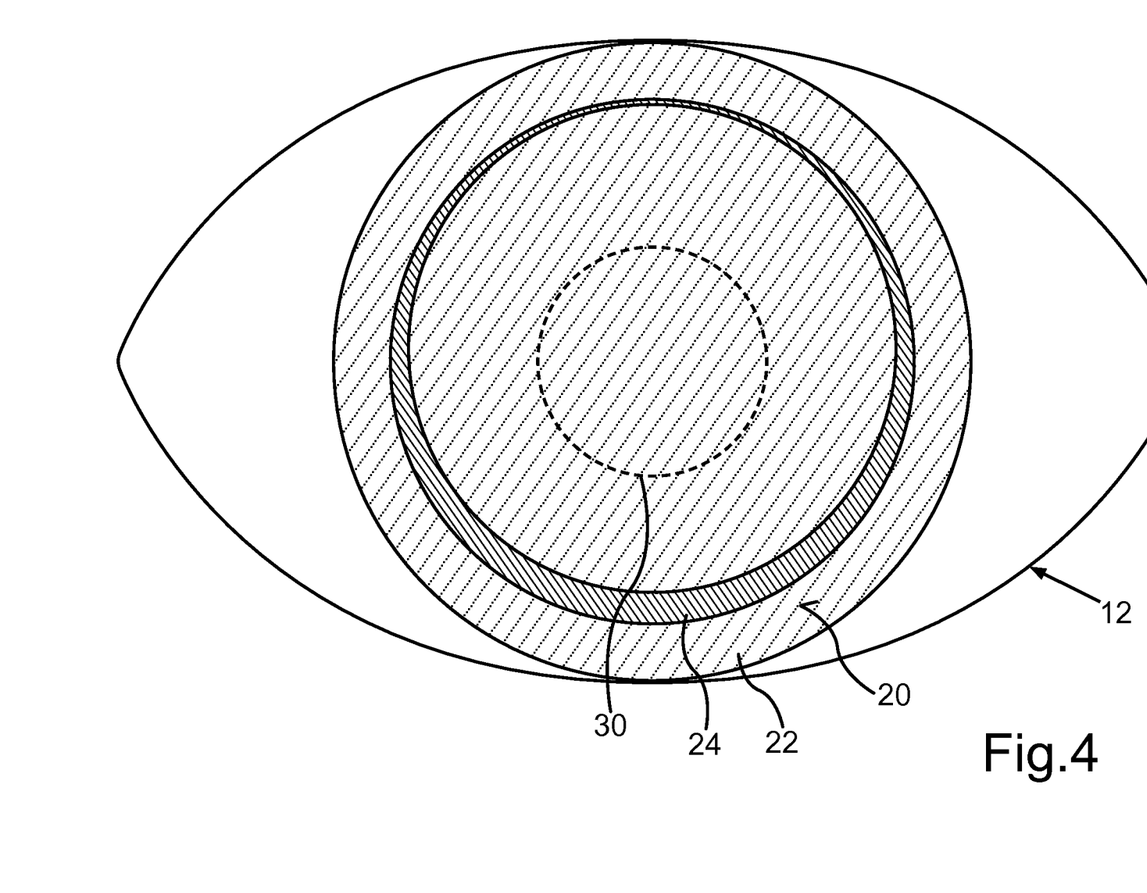

FIG. 3 shows a shape of the removed volume 24 in the surface 20 of the cornea 22 that is a closed ring. This shapes lead to a uniform strain on the cornea 22 and especially allows for a correction of a refractive error without any astigmatism. FIG. 4 shows a volume 24 that is a crescent shaped closed ring. This shape allows correction of astigmatism in the eye 12 and/or to shift its visual axis. Also, this shape of the volume 24 results in a gradual change of a strain, stress and/or tension in the surface 20 of the cornea 22 without any peaks of said strain, stress and/or tension. A peak in stress, tension and/or strain could possibly further damage the cornea 22.

Figure 5:
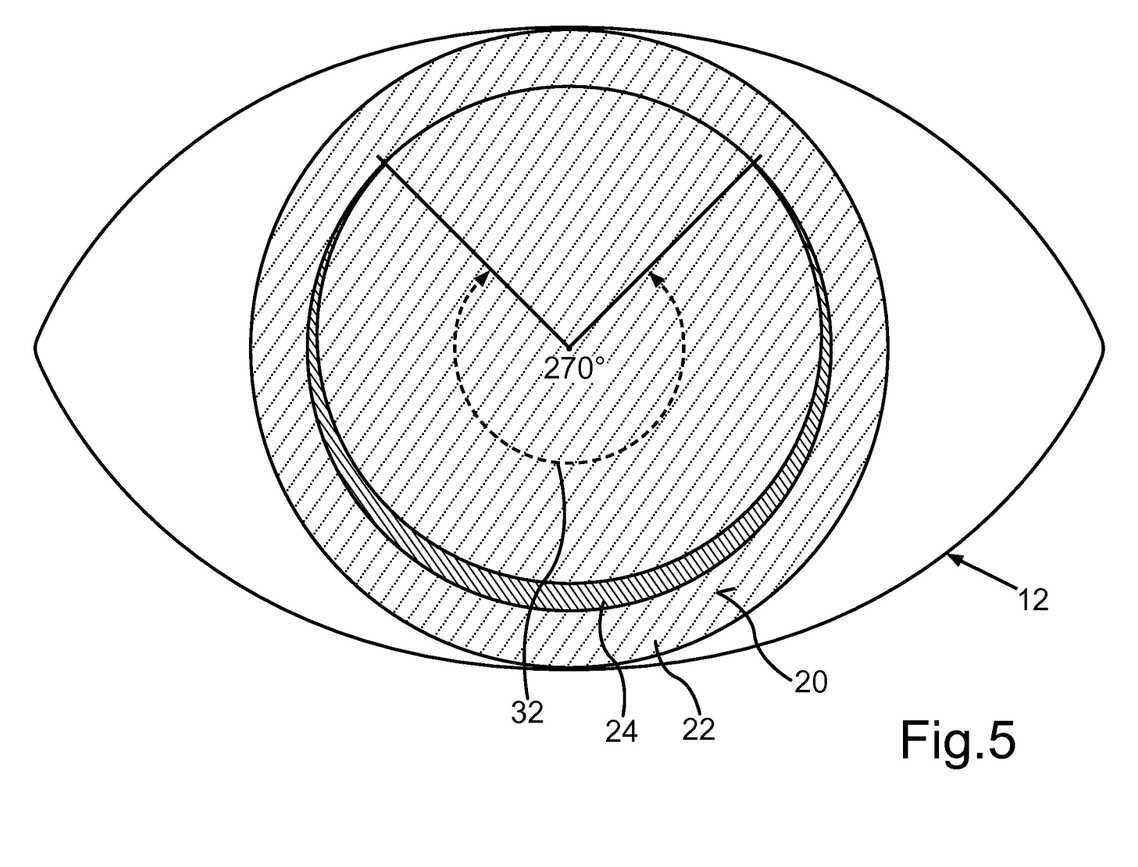
Figure 6:
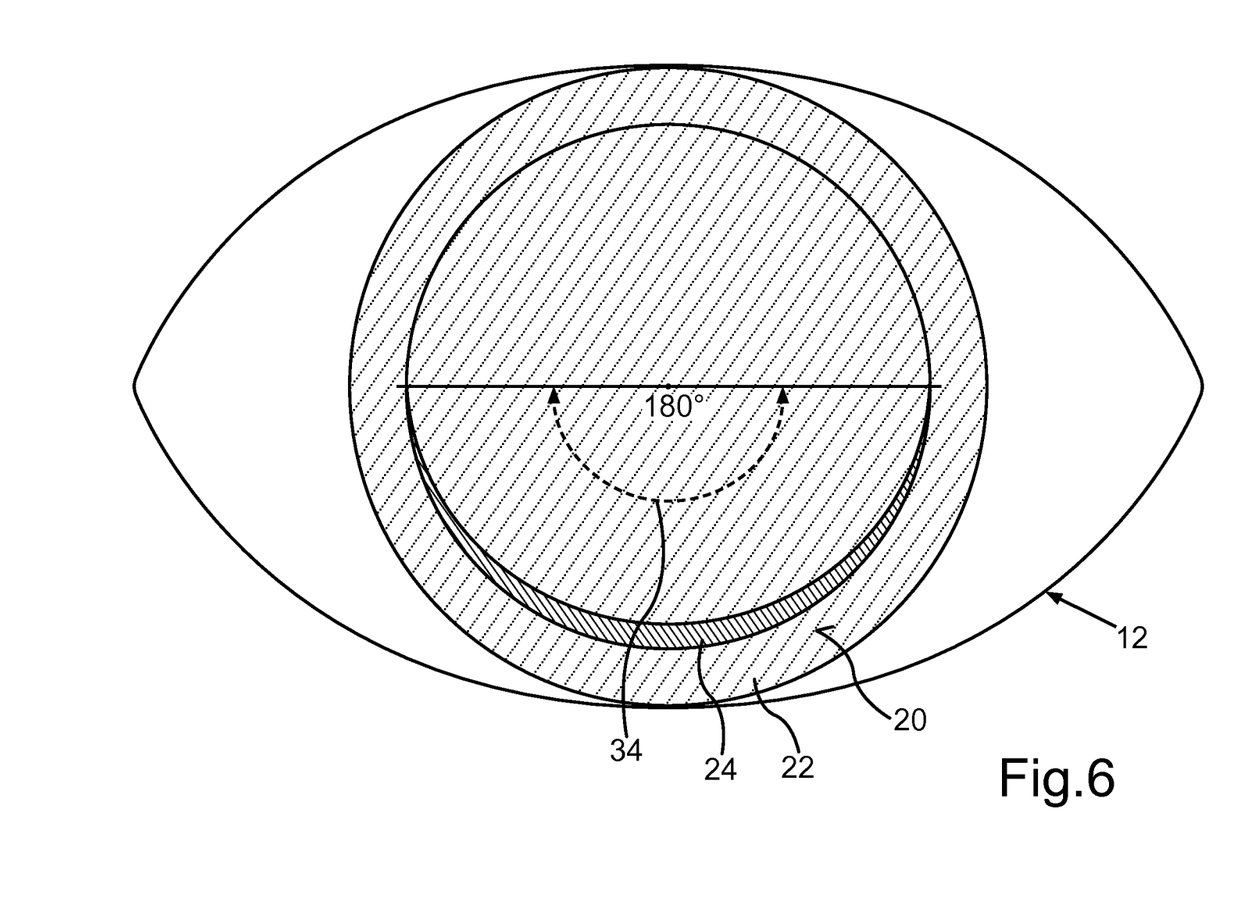
Figure 7:
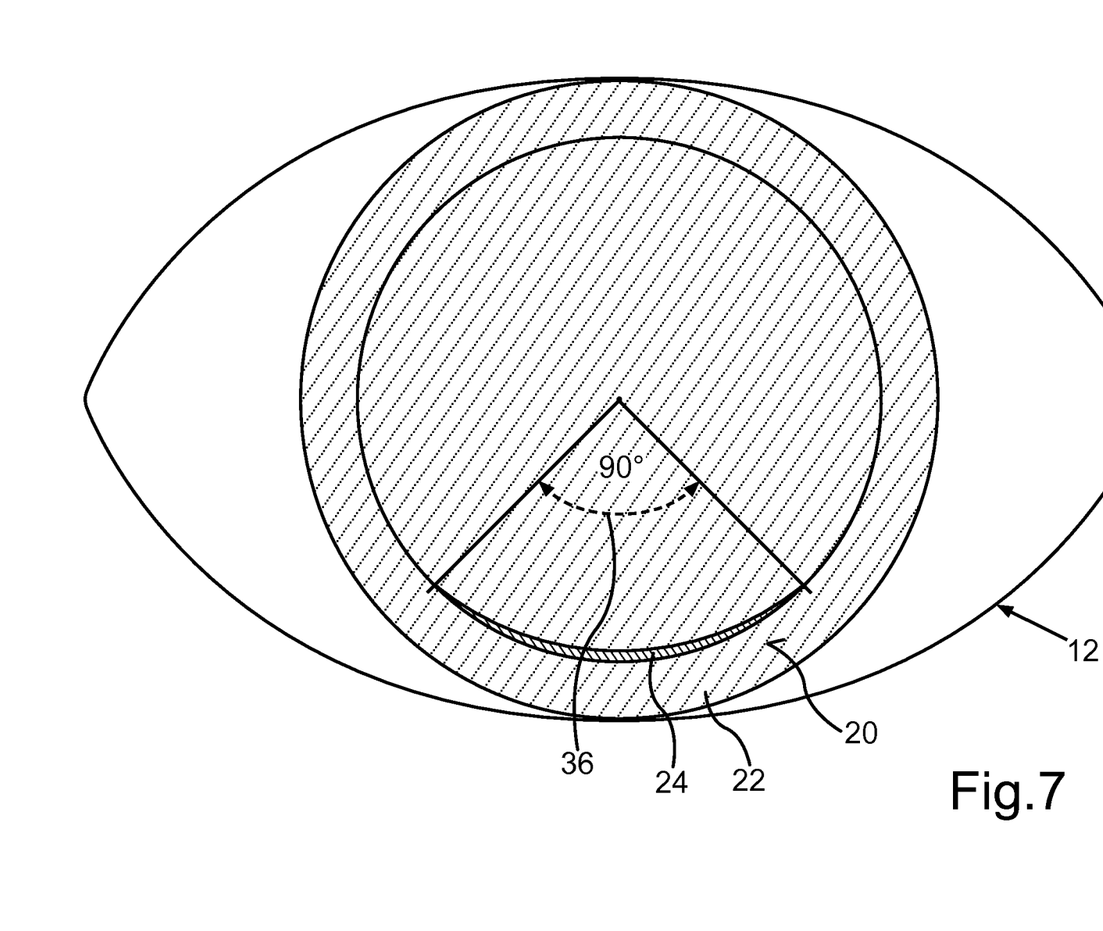

FIG. 5, FIG. 6, and FIG. 7 show a volume 24 that is a crescent. This can also be called a crescent shaped. The smaller the crescent, the smaller the volume 24 removed from the cornea 22. The crescent shape also allows correcting especially complex deformations of the cornea 22. FIG. 5 shows a volume 24 that covers a 270 degree angle along a circumference of the surface 20 of the cornea 22. This angle is indicated by arrow 32. In FIG. 6, the volume 24 only covers an angle of 180 degrees which is indicated by arrow 34. FIG. 7 shows a crescent shaped volume 24 that only covers a 90 degree angle of the surface 20 of the cornea 22, which is indicated by arrow 36.

Figure 8:
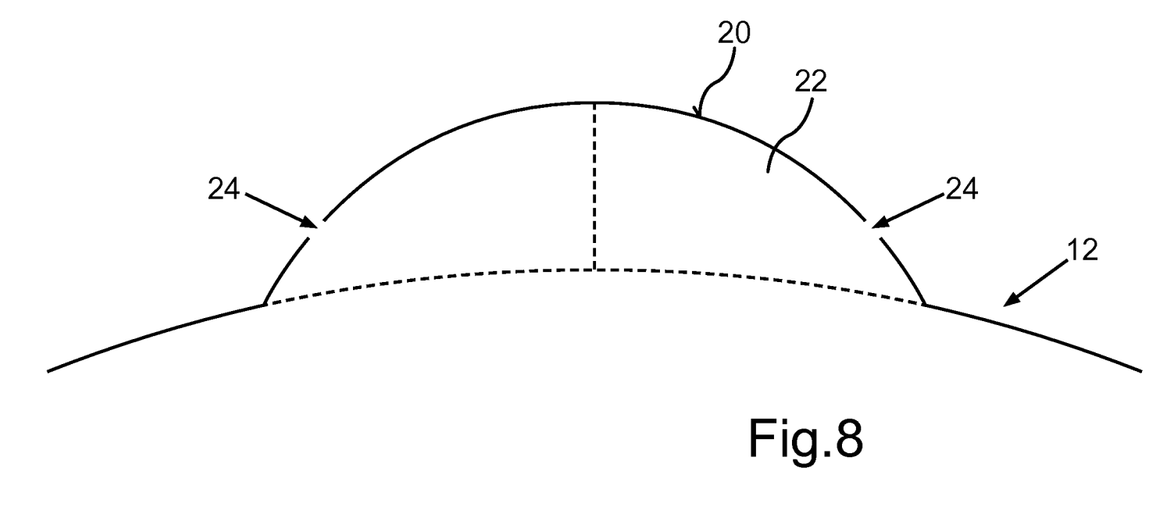
FIGS. 8 to 9 illustrate in a schematic sectional view of the eye according to FIG. 2 how its refractive error is corrected.

FIG. 8 shows in a schematic sectional view of the eye 12, where the volume 24 has been removed from the surface 20 of the cornea 22. The volume 24 has been removed from the surface 20 of the cornea 22 along a circumference of the cornea 22. The volume 24 has been removed by cutting and/or ablating the corneal tissue with the laser radiation 16 emitted by the laser device 14 and afterwards flushing the eye 12 with a saline solution.

Figure 9:
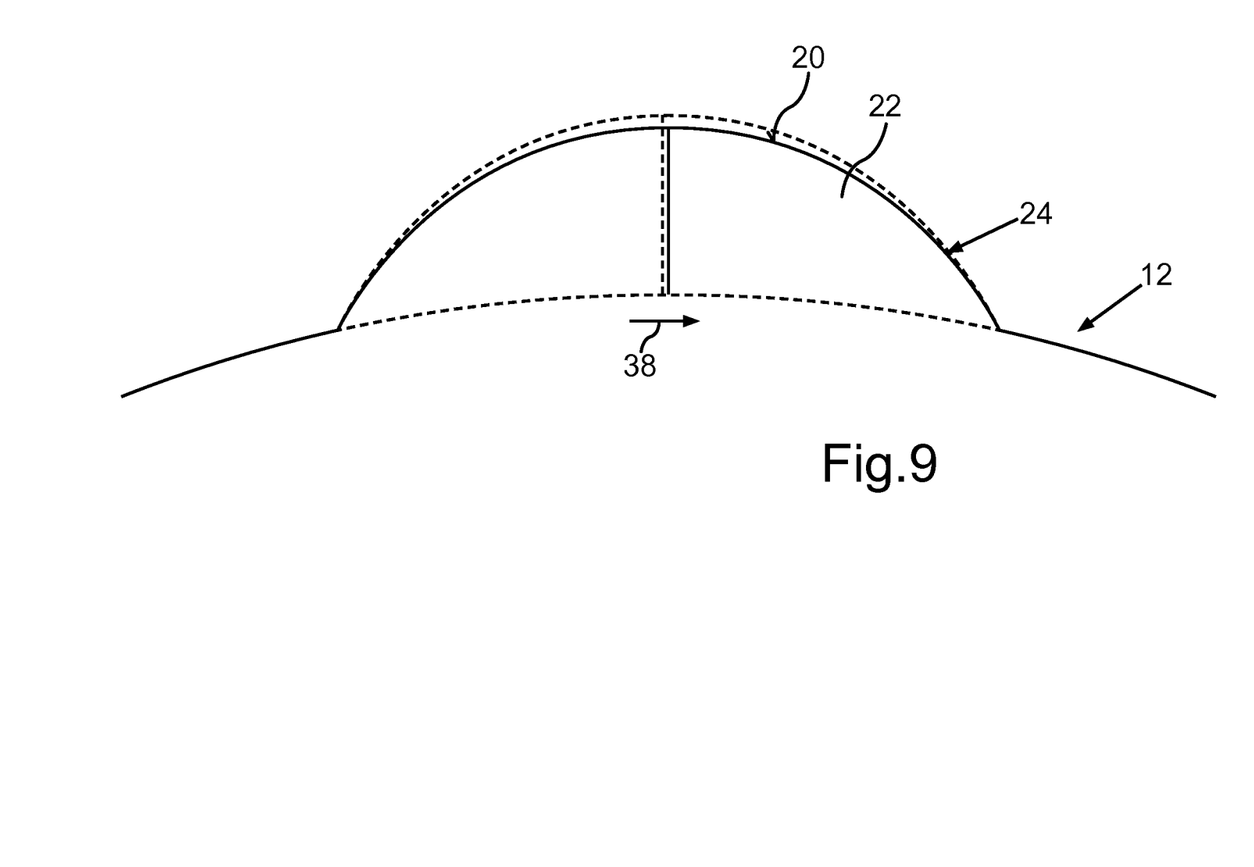

FIG. 9 illustrates in a schematic sectional view of the eye 12 how the surgical procedure has changed the refraction of the eye 12, thus at least partially correcting the refractive error of the eye 12. The openings in the surface 20 of the cornea 22 due to removal of the volume 24 have been sutured closed. After the cornea 22 has been healed, these sutures preferably are removed from the eye 12. The suturing results in the surface 20 of the cornea 22 being stretched in such a way that the cornea 22 is flattened. This decreases a radius of the cornea 22, changing its refraction. The changes have been illustrated in FIG. 9 by the dashed lines. The dashed lines in FIG. 9 show the shape of the eye 12 with its cornea 22 according to FIG. 8, before the cornea 22 has been sutured.

Furthermore, due to the volume 24 having a crescent shape, the thickest point of the cornea 22 has been shifted to one side of the eye 12. This means the visual axis of the cornea 22 has also been shifted, allowing for correction of more complex refractive errors of the eye 12. This shift is indicated in FIG. 9 by the arrow 38.

FIG. 10 to FIG. 17 show several examples of a protective mask 40 for the eye 12 during the surgical procedure, whereby each example is shown in a schematic top view and in a schematic perspective view. The mask 40 has an opening 42 corresponding to the shape resulting in the surface 20 of the cornea 22 due to the cut-out and/or ablated volume 24 and is placed on the cornea 22 of the eye 12 before the laser radiation 16 is emitted to cut and/or ablate the volume 24 out of the surface 20 of the cornea 22.

The opening 42 allows the laser radiation 16 to only cut and/or ablate the cornea 22 in an area of the opening. Where the cornea 22 is covered by the protective mask 40, the emitted laser radiation 16 is unable to cut and/or ablated the cornea 22. Thus, the eye 12 and/or the cornea 22 are protected in this area from an incorrectly aimed laser radiation 16 and/or incorrectly focused laser radiation 16. Furthermore, the laser radiation 16 can be aimed less precisely and/or focused less precisely while still achieving an especially precise cut and/or ablation. Additionally, the mask 40 can prevent any damage to the eye 12 due to unwanted movement of the eye 12 during the procedure.

Figure 10:
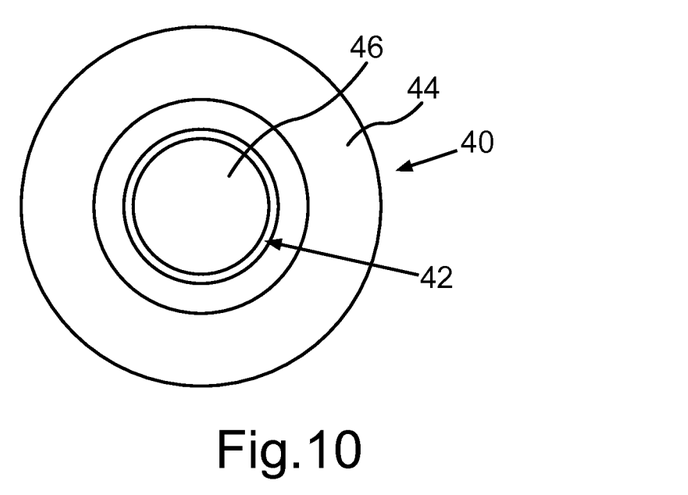
FIGS. 10 to 17 show several examples of a protective mask for an eye, whereby each example is shown in a schematic top view and in a schematic perspective view.
Figure 11:
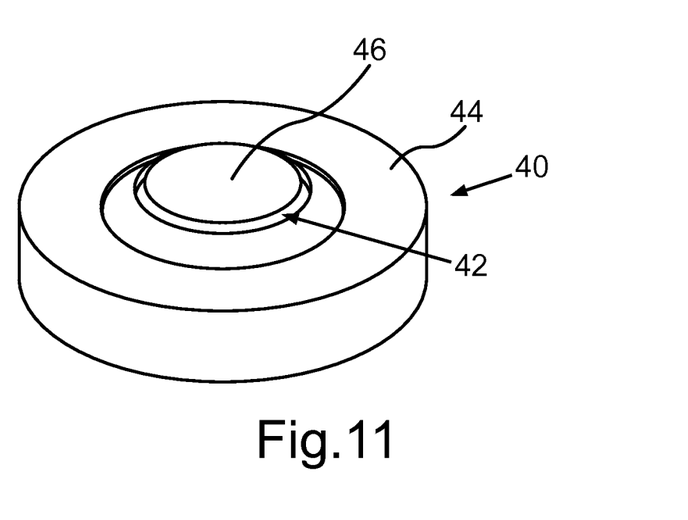

The example of the mask 40 as shown in FIG. 10 and FIG. 11 has an opening 42 that corresponds to the shape of the removed volume 24 in the surface 20 of the cornea 22 which is a closed ring, as shown in FIG. 3. In this case, the mask 40 comprises two separate parts: an outer ring 44 and an inner disk 46, which are placed separately on the eye 12 and centered to the pupil 30. The opening 42 is constituted by an empty space between the outer ring 44 and the inner disk 46 due to such a placement.

Figure 12:
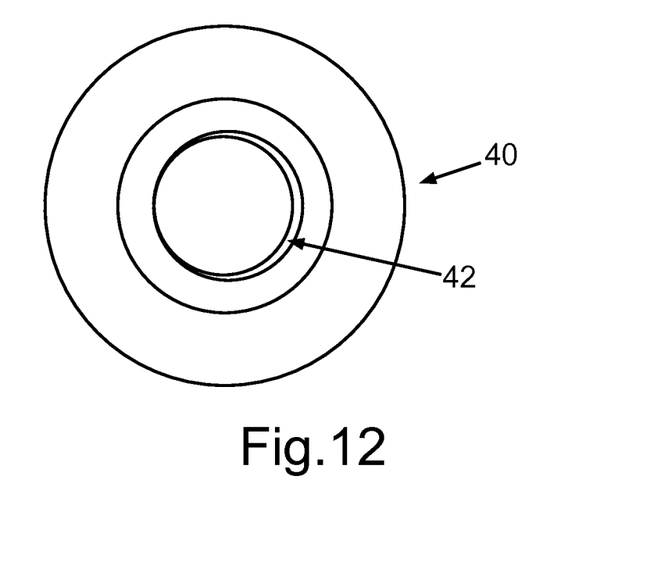
Figure 13:
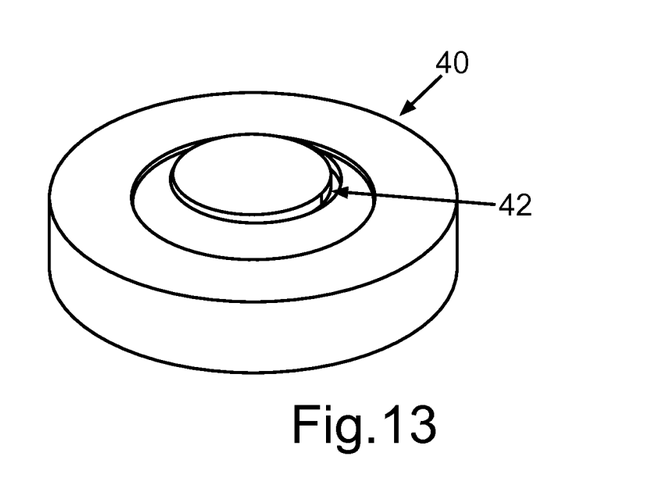

The example of the mask 40 as shown in FIG. 12 and FIG. 13 has an opening 42 that corresponds to the shape of the removed volume 24 in the surface 20 of the cornea 22 which is a crescent shaped closed ring, as shown in FIG. 4.

Figure 14:
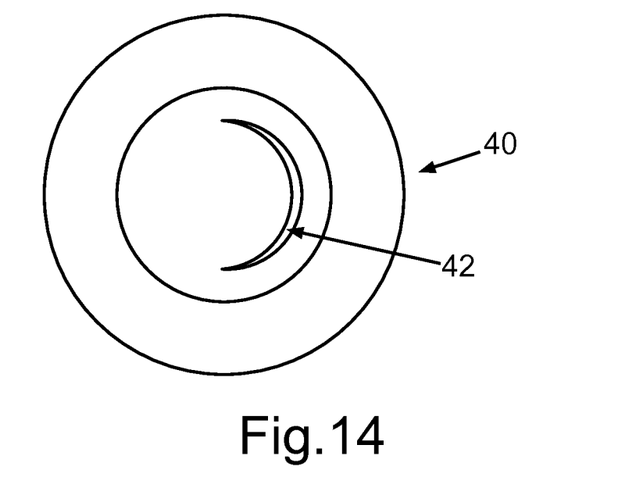
Figure 15:
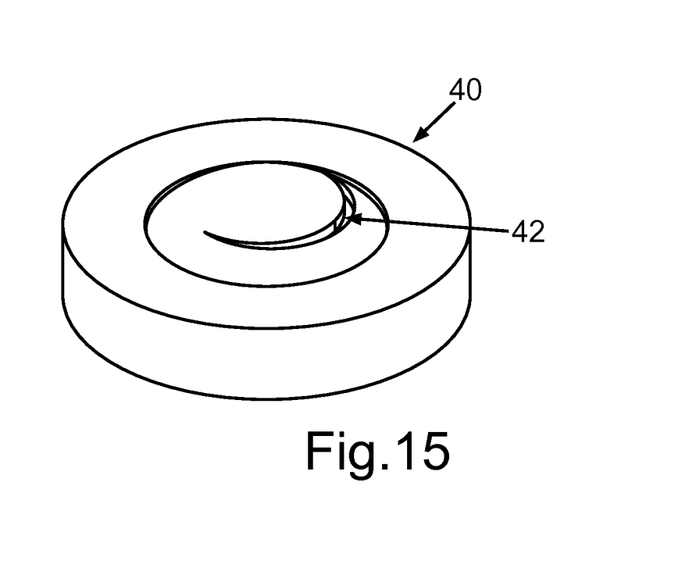
Figure 16:
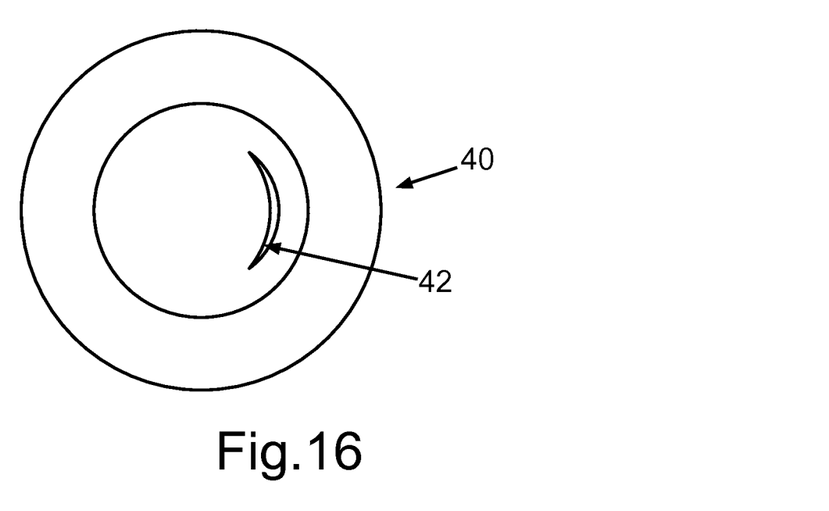
Figure 17:
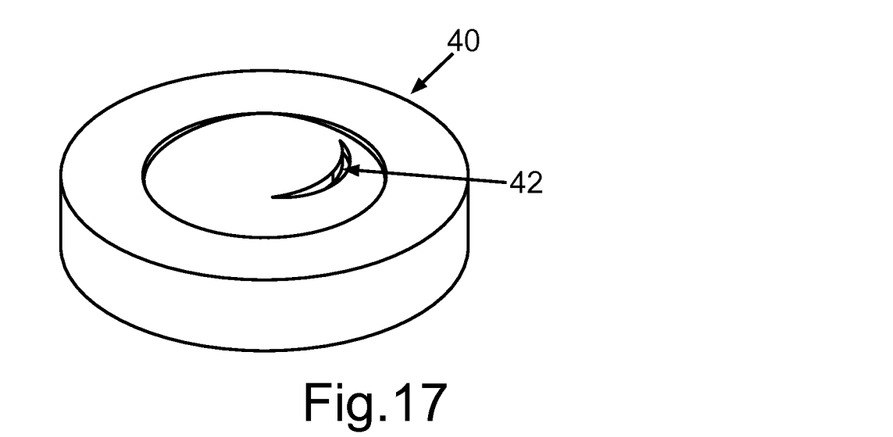

The example of the mask 40 as shown in FIG. 14 and FIG. 15 has an opening 42 that corresponds to the shape of the removed volume 24 in the surface 20 of the cornea 22 which is a crescent, as shown in FIG. 6. The opening 42 covers an angle of 180 degrees.

The example of the mask 40 as shown in FIG. 14 and FIG. 15 has an opening 42 that corresponds to the shape of the removed volume 24 in the surface 20 of the cornea 22 which is a crescent, as shown in FIG. 7. In this case, the opening 42 covers an angle of 90 degrees.

The examples of the protective mask 40 according to FIG. 12 to FIG. 17 only comprise one part. However, the protective mask 40 can also comprise two parts like the mask 40 shown in FIG. 10 and FIG. 11. The opening 42 can go completely through a body of the protective mask 40 or can only form a kind of recess in an outer surface of the protective mask 40. In the case of the opening 42 going completely through the body of the protective mask 40, any cut-out and/or ablated tissue of the cornea 22 can be removed very easily without needing to remove the protective mask 40. In the case of the opening 42 forming a kind of recess in the outer surface of the protective mask 40, the protective mask 40 is especially comfortable to wear. Also, in this case the protective mask 40 has less sharp corners that are in contact with the cornea 22 of the eye 12.

Overall the treatment apparatus 10 and the methods presented here are especially suited for correcting the refractive error of an eye 12 with a keratoconus degenerative disorder, as they are especially gentle to the cornea 22. The treatment method can be called crescentic laser assisted keratectomy, which can be abbreviated as CLAK.

What is claimed is:

1. A method for correcting a refractive error of an eye by a treatment apparatus,
comprising the steps of: measuring a pachymetry of the cornea of the eye; determining a volume to be cut out and/or ablated out of a surface of the cornea of the eye in dependency on the measured pachymetric data of the cornea and the refractive error of the eye; placing a protective mask, with at least one crescent shaped opening on the cornea of the eye before a laser radiation is emitted, to cut and/or ablate the volume out of the surface of the cornea, whereby the crescent shaped opening corresponds to a shape resulting in the surface of the cornea due to the cut-out and/or ablated volume;
controlling a laser by a controller, in electrical communication with the laser, laser radiation emission of the laser being controllable by the controller to emit the laser radiation to cut and/or ablate the volume out of the surface of the cornea; and suturing at least a portion of the cornea bordering the cut-out and/or ablated volume and stretching the surface of the cornea to flatten the cornea, whereby the cut-out and/or ablated volume in the surface of the cornea resifts in a shape of a crescent or a crescent shaped closed ring.

2. The method according to claim 1, wherein the cut-out and/or ablated volume in the cornea of the eye is closed by suturing at least two opposite sides of the cornea which are bordering the cut-out and/or ablated volume together, thus reducing a radius of the cornea.

3. The method according to claim 1, wherein the refractive error of the eye is not corrected by reshaping the lenticular shape of the cornea itself.

4. The method according to claim 1, wherein the refractive error of the eye is corrected by changing the tensions in the surface of the cornea and/or reducing the surface of the cornea.

5. The method according to claim 1, wherein the cut-out and/or ablated volume is located outside of the pupil of the eye.

6. The method according to claim 1, further comprising, measuring an intraocular pressure of the eye, with a tonometer; and
determining the volume to be cut-out and/or ablated in dependency on the measured intraocular pressure of the eye.

7. The method according to claim 1, wherein the volume to be cut-out and/or ablated is located with an equal distance to a visual axis of the eye with a cut side of the volume facing the visual axis, or with equal distance to a symmetry axis of the volume.

8. The method according to claim 1, wherein the mask is plastic.

9. The method according to claim 1, wherein the mask k configured to at least partially scatter or absorb the laser radiation from the laser.

* * * * *